(12) United States Patent
Noguchi

(10) Patent No.: US 9,036,769 B2
(45) Date of Patent: May 19, 2015

(54) RADIO TOMOGRAPHIC IMAGE GENERATION METHOD AND DEVICE

(71) Applicant: FUJIFILM Corporation, Minato-ku, Tokyo (JP)

(72) Inventor: Masafumi Noguchi, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 168 days.

(21) Appl. No.: 13/917,073

(22) Filed: Jun. 13, 2013

(65) Prior Publication Data

US 2013/0272490 A1  Oct. 17, 2013

Related U.S. Application Data

(63) Continuation of application No. PCT/JP2011/007001, filed on Dec. 14, 2011.

(30) Foreign Application Priority Data

Dec. 15, 2010 (JP) ................................. 2010-278915

(51) Int. Cl.
*G01N 23/00* (2006.01)
*G06T 11/00* (2006.01)
*A61B 6/00* (2006.01)

(52) U.S. Cl.
CPC ............. *G06T 11/006* (2013.01); *A61B 6/4441* (2013.01); *A61B 6/4464* (2013.01); *A61B 6/5223* (2013.01); *G06T 2211/424* (2013.01)

(58) Field of Classification Search
CPC ....................................................... A61B 6/032
USPC ....................................................... 378/4–20
See application file for complete search history.

(56) References Cited

U.S. PATENT DOCUMENTS

2007/0201611 A1* 8/2007 Pratx et al. ......................... 378/4
2007/0297656 A1* 12/2007 DeMan et al. ................. 382/128

(Continued)

FOREIGN PATENT DOCUMENTS

JP   2006-025868 A   2/2006
JP   2007-202700 A   8/2007

(Continued)

OTHER PUBLICATIONS

Communication dated Sep. 30, 2014 from the Japanese Patent Office in counterpart application No. 2010-278915.

(Continued)

*Primary Examiner* — Hoon Song
(74) *Attorney, Agent, or Firm* — Sughrue Mion, PLLC

(57) ABSTRACT

A radio tomographic image generation device includes a reconstruction unit for generating a plurality of reconstructed images of different iteration numbers by a successive approximation process; a region segmentation unit for obtaining information about structure based on radiographic image signals, and segmenting, based on the information about structure, a region, of which the tomographic image is generated, into a plurality of segmented regions having different information about structure; and an image combining unit for generating partial tomographic images by using the reconstructed images of different iteration numbers for the individual segmented regions based on the information about structure of the individual segmented regions, and generating a tomographic image of a subject by using the generated partial tomographic images for the individual segmented regions.

28 Claims, 6 Drawing Sheets

(56) References Cited

U.S. PATENT DOCUMENTS

2008/0159469 A1* 7/2008 Ruhrnschopf et al. ............ 378/4
2009/0086883 A1* 4/2009 Harer et al. ....................... 378/4
2009/0190814 A1   7/2009 Bouman et al.

FOREIGN PATENT DOCUMENTS

| JP | 2008-006288 A | 1/2008 |
| JP | 2009-172380 A | 8/2009 |
| WO | 2011/122613 A1 | 6/2011 |

OTHER PUBLICATIONS

International Search Report for PCT/JP2011/007001 dated Mar. 27, 2012.

* cited by examiner

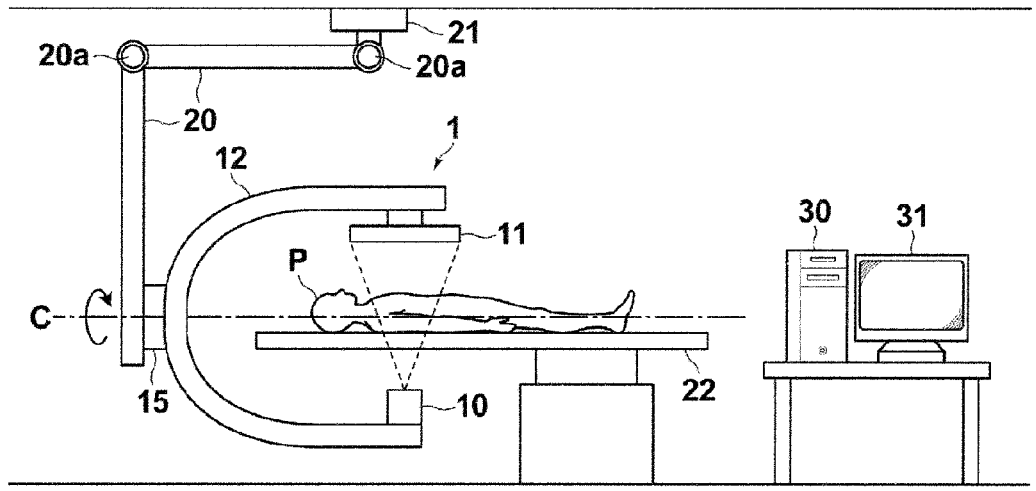
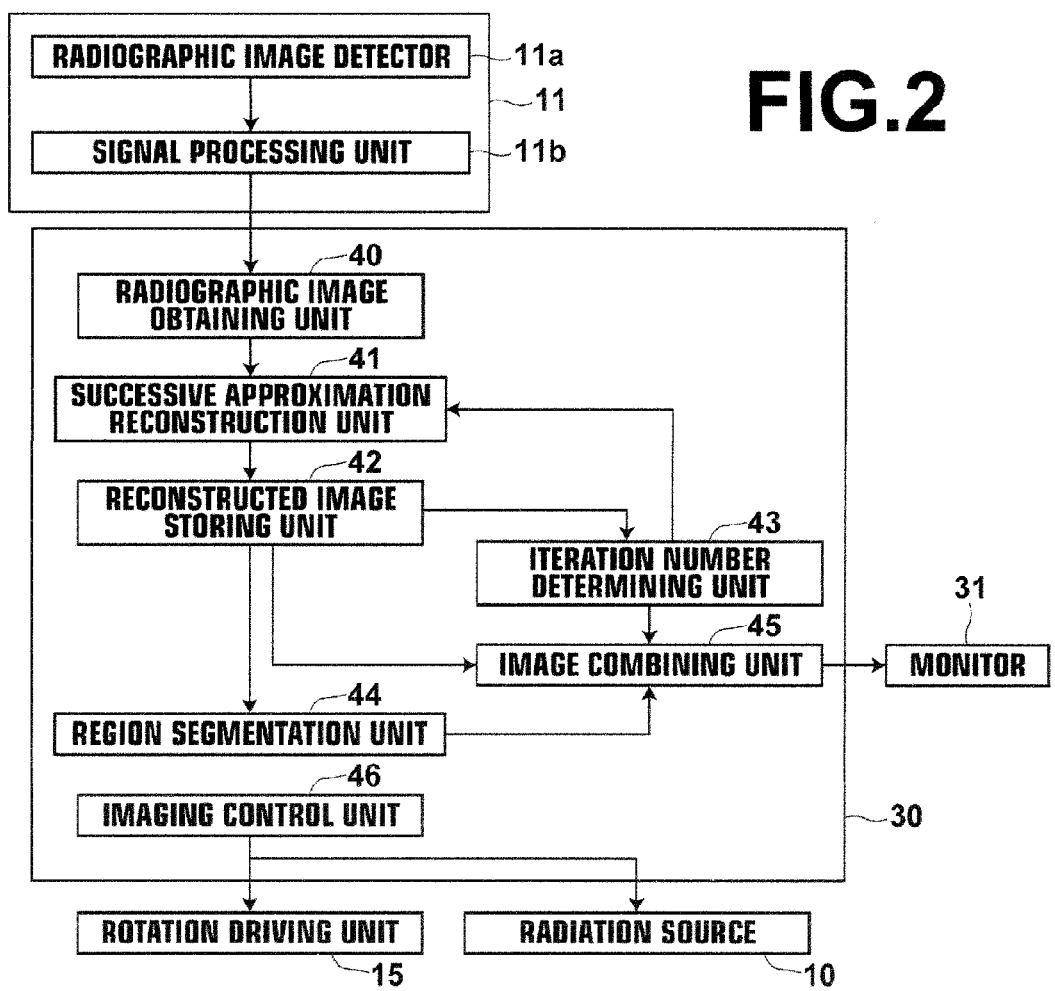

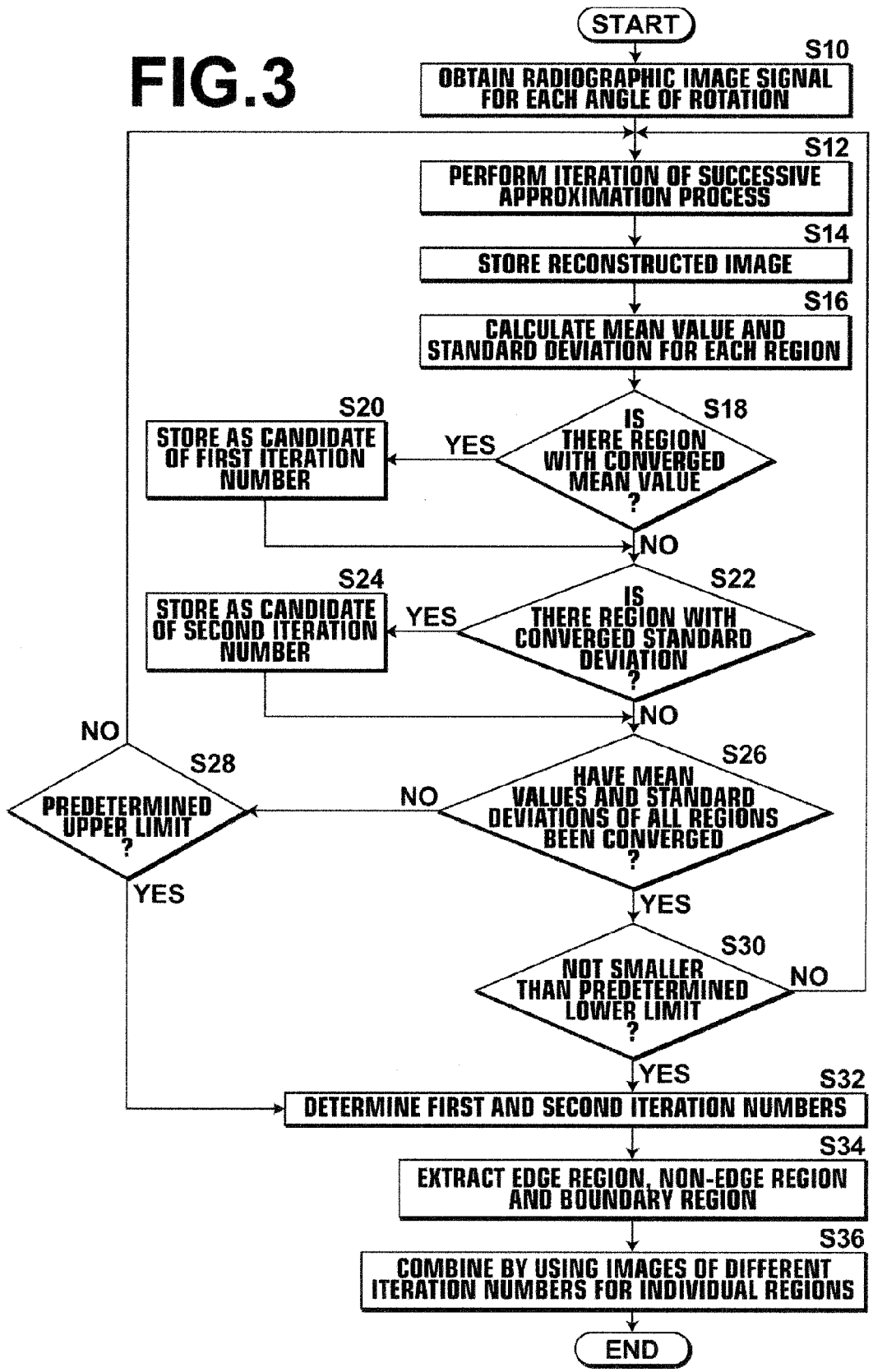

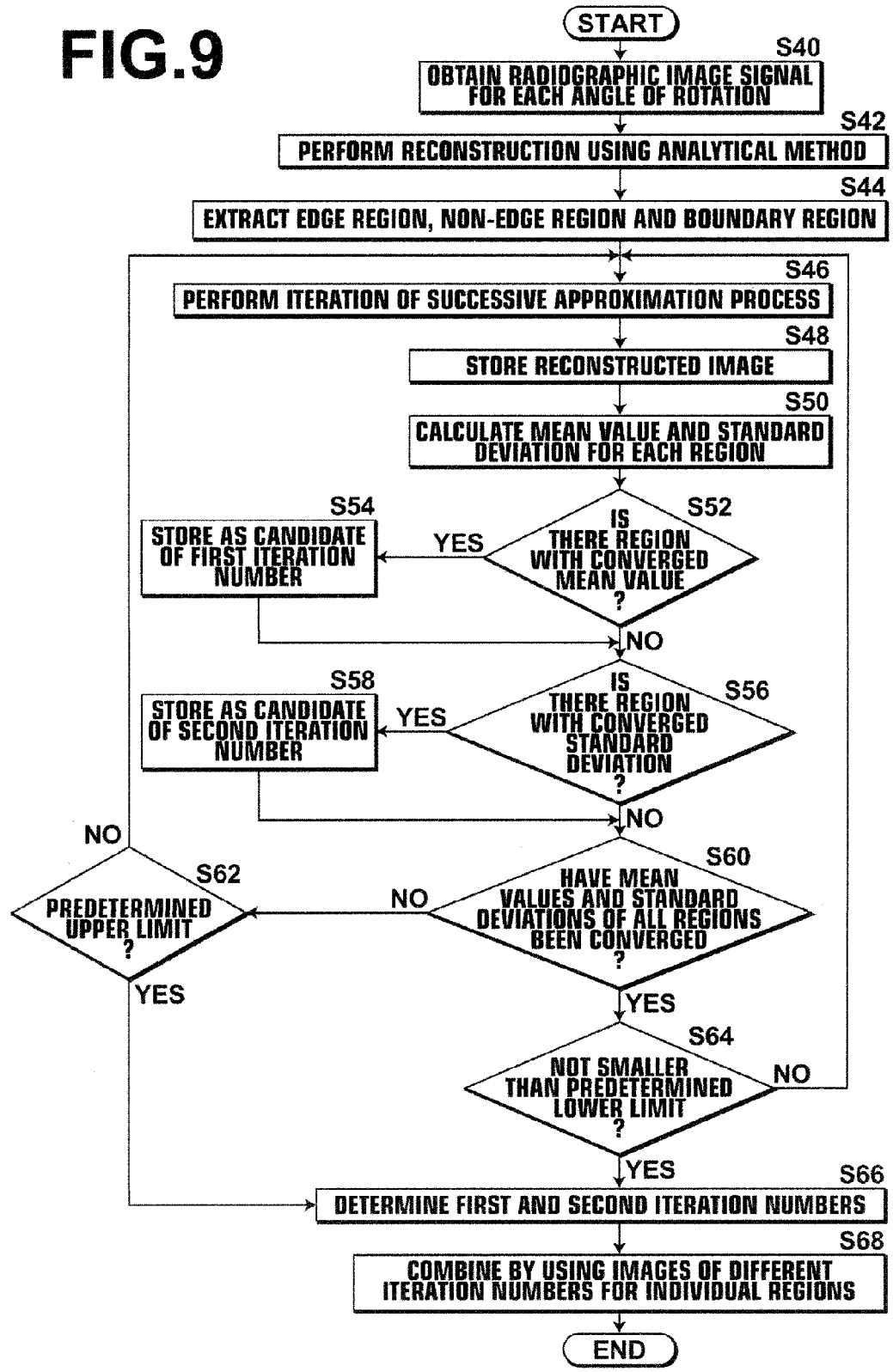

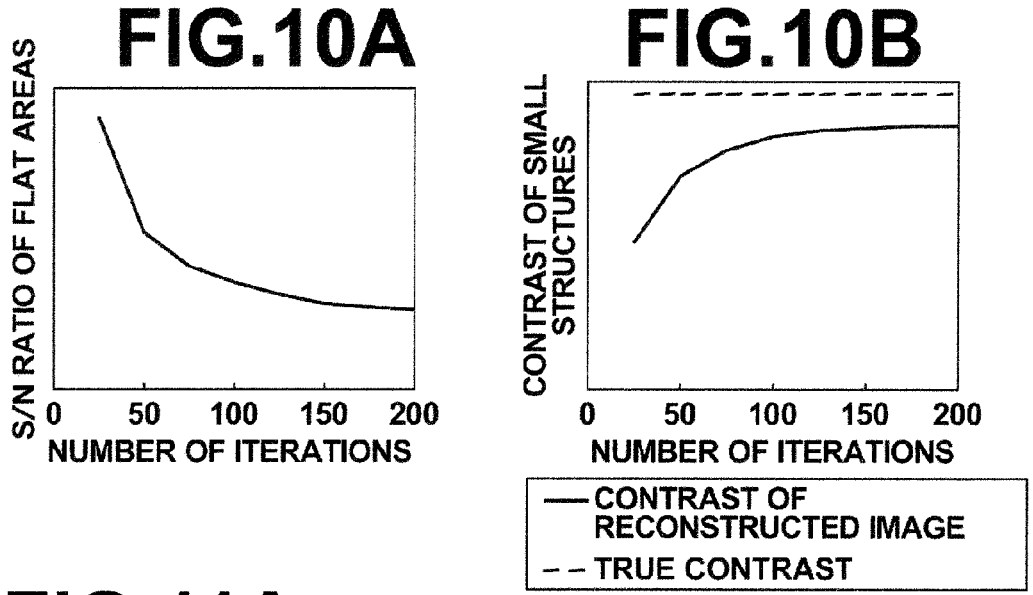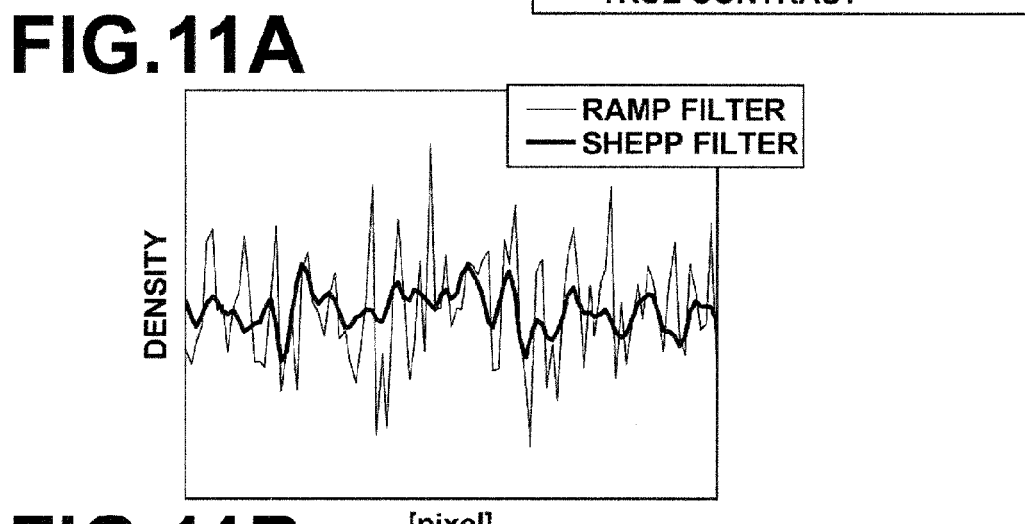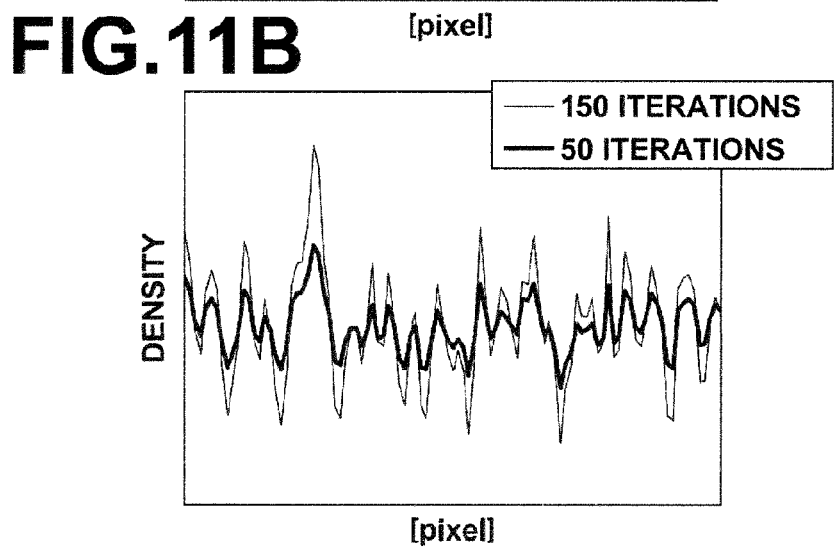

RADIO TOMOGRAPHIC IMAGE GENERATION METHOD AND DEVICE

TECHNICAL FIELD

The present invention relates to a radio tomographic image generation method and a radio tomographic image generation device for generating a tomographic image of a subject by making a radiographic image detector orbit around the subject to obtain a radiographic image signal at each predetermined imaging angle, and performing reconstruction processing based on the radiographic image signals at the individual imaging angles.

BACKGROUND ART

Conventionally, radio tomographic imaging and displaying systems are widely used in clinical practice. In such a radio tomographic imaging and displaying system, a radiation source and a radiographic image detector are disposed to face each other via a subject, and the set of the radiation source and the radiographic image detector are made to orbit around the subject to take radiographic images with applying radiation from various angles, and a tomographic image is reconstructed using the radiographic images taken at the individual angles to display an arbitrary slice.

An example of a method for reconstructing a tomographic image for use with the above-described radio tomographic imaging and displaying system is a successive approximation process, where linear absorption coefficients in a slice are modeled with a matrix and solved using a statistical way of thinking.

The successive approximation process is a reconstruction method where a tomographic image of interest is obtained by repeating an iteration based on radiographic images taken at individual imaging angles. Reconstruction methods which are usually referred to as an algebraic approach or statistical approach fall under the successive approximation process, and examples thereof include the ML-EM (Maximum Likelihood—Expectation Maximization) method and the OS-EM (Ordered Subsets Expectation Maximization) method.

DISCLOSURE OF INVENTION

With the above-described successive approximation process, sharpness of the obtained tomographic image is improved and the image approaches to the true solution by repeating the iteration more and more. However, if the radiographic images before subjected to the iteration include noise, the noise is gradually increased as the number of iterations increases.

FIG. 10A shows S/N ratios of a flat area in a radiographic image along with the increase of the number of iterations, and FIG. 10B shows change of the contrast of a small structure, such as a calcification, in a radiographic image along with the increase of the number of iterations.

When the successive approximation process is used, it is desirable to increase the number of iterations as much as possible in view of the sharpness and the accuracy of solution. However, as the number of iterations increases, noise of a region like a flat area, such as the interior of an organ, which does not require high sharpness, is increased, as shown in FIG. 10A. If the number of iterations is decreased to obtain high S/N of a flat area, the entire image is blurred, resulting in a tomographic image with poor sharpness of edges and contrast of calcification, etc. That is, when the successive approximation process is used, there is a trade-off between the sharpness and contrast of small structures and the S/N of flat areas, and it is difficult to obtain a tomographic image with high sharpness and contrast of small structures and high S/N of flat areas.

Japanese Unexamined Patent Publication No. 2007-202700 (hereinafter, Patent Document 1) proposes a method for generating a reconstructed image using the FBP (Filter Back Projection) method rather than the successive approximation process, wherein different reconstruction functions are defined for different parts, such as heart, lungs, soft tissues and bones, a plurality of reconstructed images are generated using the different reconstruction functions and the reconstructed images are combined. Patent Document 1 proposes nothing about the problem unique to the successive approximation process, as described above, and a solution thereof.

In view of the above-described circumstances, the present invention is directed to providing a radio tomographic image generation method and a radio tomographic image generation device for generating a tomographic image by performing reconstruction using a successive approximation process, which allow improvement of the sharpness and contrast of small structures and the S/N ratio of flat areas.

A radio tomographic image generation device of the invention is a radio tomographic image generation device including: a radiographic image obtaining unit, wherein at least one of a radiation source and a radiographic image detector for detecting radiation emitted from the radiation source and transmitted through a subject to output a radiographic image signal representing a radiographic image of the subject is made to orbit around the subject to obtain the radiographic image signal for each predetermined imaging angle outputted from the radiographic image detector when the radiation is applied to the subject at the predetermined imaging angle; and a tomographic image generation unit for generating a tomographic image of the subject by performing reconstruction using a successive approximation process based on the radiographic image signals for the individual imaging angles obtained by the radiographic image obtaining unit, wherein the tomographic image generation unit includes: a reconstruction unit for generating a plurality of reconstructed images of different iteration numbers of the successive approximation process; a region segmentation unit for obtaining information about structure based on the radiographic image signals segmenting, based on the information about structure, a region, of which the tomographic image is generated, into a plurality of segmented regions having different information about structure; and an image combining unit for generating partial tomographic images by using the reconstructed images of different iteration numbers for the individual segmented regions segmented by the segmentation unit based on the information about structure of the individual segmented regions, and generating the tomographic image of the subject by using the generated partial tomographic images for the individual segmented regions.

In the above-described radio tomographic image generation device of the invention, the information about structure may be edge information, and the region segmentation unit may calculate an edge likelihood index value based on the edge information, may determine a region as being an edge region if the index value of the region is greater than a predetermined threshold, may determine a region as a non-edge region if the index value of the region is not greater than the threshold, and may perform the region segmentation wherein the segmented regions are the edge region and the non-edge region.

The information about structure may represent an edge structure detected by a morphology operation, and the region segmentation unit may determine a region of the edge structure as being an edge region, may determine a region other than the region of the edge structure as being a non-edge region, and may perform the region segmentation wherein the segmented regions are the edge region and the non-edge region.

The region segmentation unit may determine a region including a boundary line between the edge region and the non-edge region and having a predetermined width as being a boundary region, and may perform the region segmentation wherein the segmented regions are the edge region, the non-edge region and the boundary region.

The information about structure may be edge information, and the region segmentation unit may calculate an edge likelihood index value based on the edge information, may determine a region as being a non-edge region if the index value of the region is not greater than a first threshold, may determine a region as being an edge region if the index value of the region is greater than a second threshold, which is greater than the first threshold, may determine a region as being a boundary region if the index value of the region is greater than the first threshold and not greater than the second threshold, and may perform the region segmentation wherein the segmented regions are the edge region, the non-edge region and the boundary region.

The tomographic image generation unit may further include an iteration number determining unit, the iteration number determining unit including a plurality of iteration number determining regions set therein, the iteration number determining regions being defined by segmenting a region, of which the tomographic image is generated, into a plurality of regions, and the iteration number determining regions being used for determining the iteration numbers of the reconstructed images used to generate the partial tomographic images, wherein the iteration number determining unit may obtain, for each iteration number determining region, information about degree of convergence of the iteration by using the reconstructed images generated by the reconstruction unit, and may determine, based on the obtained information about degree of convergence, the iteration number of the reconstructed image used to generate the partial tomographic image for each iteration number determining region, and wherein the image combining unit may generate the partial tomographic image for each segmented region based on the reconstructed image of the iteration number determined for the iteration number determining region corresponding to the segmented region.

The iteration number determining unit may obtain a plurality of pieces of the information about degree of convergence for each iteration number determining region, and may determine a first iteration number and a second iteration number greater than the first iteration number based on the obtained prices of the information about degree of convergence, and the image combining unit may generate the partial tomographic image of each segmented region by using the reconstructed image of an iteration number not smaller than the first iteration number and not greater than the second iteration number determined for the iteration number determining region corresponding to the segmented region.

The pieces of information about degree of convergence may be pieces of information about degree of convergence of mean value and degree of convergence of standard deviation of the individual reconstructed images in the iteration number determining region, and the iteration number determining unit may determine the first iteration number based on the pieces of information about degree of convergence of mean value, and may determine the second iteration number based on the pieces of information about degree of convergence of standard deviation.

The image combining unit may generate the partial tomographic image for the segmented region which is the edge region by using the reconstructed image of the second iteration number, and may generate the partial tomographic image for the segmented region which is the non-edge region by using the reconstructed image of the first iteration number.

The image combining unit may generate the partial tomographic image for the segmented region which is the edge region by using the reconstructed image of the second iteration number, may generate the partial tomographic image for the segmented region which is the non-edge region by using the reconstructed image of the first iteration number, and may generate the partial tomographic image for the segmented region which is the boundary region by using the reconstructed image of an iteration number smaller than the second iteration number and greater than the first iteration number.

The image combining unit may generate the partial tomographic image for the segmented region which is the edge region by using the reconstructed image of the second iteration number, may generate the partial tomographic image for the segmented region which is the non-edge region by using the reconstructed image of the first iteration number, and may generate the partial tomographic image for the segmented region which is the boundary region by using the reconstructed image of an iteration number nearer to the second iteration number for the boundary region nearer to the edge region or using the reconstructed image of an iteration number nearer to the first iteration number for the boundary region nearer to the non-edge region.

The image combining unit may generate the partial tomographic image for the segmented region which is the edge region by using the reconstructed image of the second iteration number, may generate the partial tomographic image for the segmented region which is the non-edge region by using the reconstructed image of the first iteration number, and may generate the partial tomographic image for the segmented region which is the boundary region by using a reconstructed image resulting from weighted sum of the tomographic image of the first iteration number and the tomographic image of the second iteration number with setting a larger weight on the tomographic image of the second iteration number for the boundary region nearer to the edge region or setting a larger weight on the tomographic image of the first iteration number for the boundary region nearer to the non-edge region.

The image combining unit may generate the partial tomographic image for the segmented region which is the edge region by using the reconstructed image of the second iteration number, may generate the partial tomographic image for the segmented region which is the non-edge region by using the reconstructed image of the first iteration number, and may generate the partial tomographic image for the segmented region which is the boundary region by using a reconstructed image of an iteration number nearer to the first iteration number for the boundary region with the index value nearer to the first threshold or using a reconstructed image of an iteration number nearer to the second iteration number for the boundary region with the index value nearer to the second threshold.

The image combining unit may generate the partial tomographic image for the segmented region which is the edge region by using the reconstructed image of the second iteration number, may generate the partial tomographic image for the segmented region which is the non-edge region by using the reconstructed image of the first iteration number, and may generate the partial tomographic image for the segmented region which is the boundary region by using a reconstructed image resulting from weighted sum of the tomographic image of the first iteration number and the tomographic image of the second iteration number with setting a larger weight on the reconstructed image of the first iteration number for the boundary region with the index value nearer to the first threshold or setting a larger weight on the reconstructed image of the first iteration number for the boundary region with the index value nearer to the second threshold.

The region segmentation unit may obtain the edge information based on the reconstructed image of the second iteration number.

The iteration number determining unit may determine the first and second iteration numbers such that the first iteration number is not smaller than a predetermined lower limit and the second iteration number is not greater than a predetermined upper limit.

The reconstruction unit may end the iteration when the second iteration numbers have been determined during generation of the reconstructed images forming the partial tomographic images of the individual segmented regions.

The iteration number determining unit may determine a candidate of the first iteration number and a candidate of the second iteration number for each of the iteration number determining regions, and then may determine a mean value, a maximum value or a minimum value of the candidates of the first iteration number of the individual iteration number determining regions as the first iteration number and a mean value, a maximum value or a minimum value of the candidates of the second iteration number of the individual iteration number determining regions as the second iteration number.

The iteration number determining regions may be regions defined by segmenting a region, of which the tomographic image is generated, into a mesh pattern.

The region segmentation unit may obtain the information about structure based on the reconstructed images obtained by an analytical method using the radiographic image signals.

The edge information may be calculated from primary differential values.

The edge information may be calculated from secondary differential values.

The edge information may be calculated from a standard deviation.

The edge information may be calculated from values resulting from band-pass filtering or values resulting from high-pass filtering.

It should be noted that the "edge information" includes not only information about an edge extending as a line but also information about a point structure.

Further, the "edge structure" includes not only an edge extending as a line but also a point structure.

A radio tomographic image generation method of the invention is a radio tomographic image generation method, wherein at least one of a radiation source and a radiographic image detector for detecting radiation emitted from the radiation source and transmitted through a subject to output a radiographic image signal representing a radiographic image of the subject is made to orbit around the subject to obtain the radiographic image signal for each predetermined imaging angle outputted from the radiographic image detector when the radiation is applied to the subject at the predetermined imaging angle, and a tomographic image of the subject is generated by performing reconstruction using a successive approximation process based on the radiographic image signals for the individual imaging angles, the method including: generating a plurality of reconstructed images of different iteration numbers of the successive approximation process; segmenting, based on the radiographic image signals, a region, of which the tomographic image is generated, into a plurality of segmented regions having different information about structure; generating partial tomographic images by using the reconstructed images of different iteration numbers for the individual segmented regions based on the information about structure of the individual segmented regions; and generating the tomographic image of the subject by using the generated partial tomographic images for the individual segmented regions.

According to the radio tomographic image generation method and device of the invention, a plurality of reconstructed images of different iteration numbers of the successive approximation process are generated. A region, of which the tomographic image is generated, is segmented into a plurality of segmented regions having different information about structure, and partial tomographic images are generated by using the reconstructed images of different iteration numbers for the individual segmented regions based on the information about structure of the individual segmented regions. Then, the tomographic image of the subject is generated by using the generated partial tomographic images for the individual segmented regions. This allows assigning, to each of the segmented regions containing different structures, the reconstructed image of an iteration number depending on the structure. For example, the reconstructed image of a relatively large iteration number can be assigned to the segmented region including small structures and the reconstructed image of a relatively small iteration number can be assigned to the segmented region that is a flat area, thereby allowing generation of a tomographic image having improved sharpness and contrast of small structures and improved S/N ratio of flat areas.

Further, while present the invention is designed for use with a successive approximation process, Patent Document 1 proposes a method for generating a tomographic image by performing reconstruction using the FBP method, wherein images reconstructed using different filter functions for individual regions are combined, as mentioned above. Now, a problem of the technique disclosed in Patent Document 1 and the advantage of the present invention are discussed.

In the case where different reconstructed images are combined, as in the technique disclosed in Patent Document 1 and in the present invention, the combined tomographic image appears unnatural unless the reconstructed images have the same level of graininess (such as the size of grainy structures, such as noise, sharpness, etc.)

When different filter functions are used for different regions in the FBP method, as in the technique disclosed in Patent Document 1, not only the magnitude of noise but also the frequency characteristics vary, and the reconstructed images have different graininess patterns. FIG. 11A shows pixel values of a tomographic image reconstructed using a Ramp filter and a tomographic image reconstructed using a Shepp filter.

In contrast, with the successive approximation process, different numbers of iterations result in different magnitudes of noise and the same graininess pattern, as shown in FIG. 11B. Therefore, when images of different iteration numbers are combined, the resulting tomographic image is less unnatural than the tomographic image provided by the technique disclosed in Patent Document 1.

BRIEF DESCRIPTION OF THE DRAWINGS

FIG. 1 is a diagram illustrating the schematic configuration of a radio tomographic imaging and displaying system employing a radio tomographic imaging device according to a first embodiment of the present invention, FIG. 2 is a block diagram illustrating the internal configuration of a radiation detector unit and a computer of the radio tomographic imaging and displaying system employing the radio tomographic imaging device according to the first embodiment of the invention, FIG. 3 is a flow chart for explaining operation of the radio tomographic imaging and displaying system employing the radio tomographic imaging device according to the first embodiment of the invention, FIG. 9 is a flow chart for explaining operation of the radio tomographic imaging and displaying system employing the radio tomographic imaging device according to the second embodiment of the invention, FIG. 10A is a graph showing one example of a relationship between the number of iterations and the S/N ratio of flat areas in a successive approximation process, FIG. 10B is a graph showing one example of a relationship between the number of iterations and the contrast of small structures in the successive approximation process, FIG. 11A is a diagram showing one example of reconstructed images based on two different functions using the FBP method, and FIG. 11B is a diagram showing one example of reconstructed images of two different iteration numbers using the successive approximation process.

DESCRIPTION OF PREFERRED EMBODIMENTS

Figure 4:
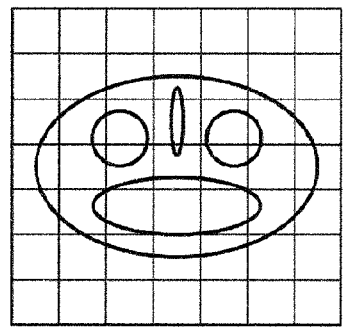
FIG. 4 is a diagram for explaining one example of iteration number determining regions that are set in the radio tomographic imaging and displaying system employing the radio tomographic imaging device according to the first embodiment of the invention.

Hereinafter, a radio tomographic imaging and displaying system employing a radio tomographic image generation device according to a first embodiment of the invention will be described with reference to the drawings. The radio tomographic imaging and displaying system is characterized by the method for generating a tomographic image; however, first, the schematic configuration of the entire radio tomographic imaging and displaying system is described. FIG. 1 illustrates the schematic configuration of the radio tomographic imaging and displaying system.

As shown in FIG. 1, the radio tomographic imaging and displaying system includes: an imaging device 1 for performing radiographic imaging of a subject P; a bed 22 serving as a table for supporting the subject P; a computer 30 connected to the imaging device 1 to control the imaging device 1 and process radiographic image signals obtained through imaging; and a monitor 31 connected to the computer 30.

The imaging device 1 includes: a radiation source 10 for emitting a conical radiation beam; a radiation detector unit 11 for detecting radiation emitted from the radiation source 10; a C-arm 12 for holding the radiation source 10 and the radiation detector unit 11, which are disposed at opposite ends of the C-arm to face each other; a rotation driving unit 15 for rotating the C-arm 12; and an arm 20 for holding the rotation driving unit 15.

The C-arm 12 is attached to the rotation driving unit 15 to be 360° rotatable about an axis of rotation C. The arm 20 includes movable parts 20a, and is held by a base 21 that is movably mounted on the ceiling. The C-arm 12 is movable to a wide range of positions in an imaging chamber via movement of the base 21, and the direction of rotation (the angle of axis of rotation) is changeable via movement of the movable parts 20a of the arm 20.

The radiation source 10 and the radiation detector unit 11 are disposed to face each other via the axis of rotation C. When a radio tomographic imaging operation is performed, the C-arm 12 is rotated by the rotation driving unit 15 by an angle in the range from 180° to 360° in a state where the positional relationship among the axis of rotation C, the radiation source 10 and the radiation detector unit 11 is fixed.

FIG. 2 is a block diagram illustrating the schematic internal configuration of the radiation detector unit 11 and the computer 30.

As shown in FIG. 2, the radiation detector unit 11 includes: a radiographic image detector 11a for generating electric charges when exposed to radiation transmitted through the subject P and outputting a radiographic image signal representing a radiographic image of the subject P; and a signal processing unit 11b for performing predetermined signal processing on the radiographic image signal outputted from the radiographic image detector 11a.

The radiographic image detector 11a is capable of repeated use for recording and reading of a radiographic image. The radiographic image detector 11a may be a so-called direct-type radiographic image detector, which directly generates electric charges when exposed to the radiation, or a so-called indirect-type radiographic image detector, which once converts the radiation into visible light, and then converts the visible light into electric charge signals. As the reading system to read out the radiographic image signal, it is desirable to use a so-called TFT reading system, where the radiographic image signals is read out by turning on and off TFT (thin film transistor) switches; however, this is not intended to limit the invention, and one of the other reading systems may be used.

The signal processing unit 11b includes an amplifier unit, which includes a charge amplifier for converting the electric charge signals read out from the radiographic image detector 11a into voltage signals, etc., an AD converter unit for converting the voltage signals outputted from the amplifier unit into digital signals, etc.

The computer 30 includes a central processing unit (CPU), a storage device, such as a semiconductor memory, a hard disk or a SSD, etc., and these hardware devices form a radiographic image obtaining unit 40, a successive approximation reconstruction unit 41, a reconstructed image storing unit 42, an iteration number determining unit 43, a region segmentation unit 44, an image combining unit 45 and an imaging control unit 46.

The radiographic image obtaining unit 40 obtains the radiographic image signal detected by the radiographic image detector 11a when the radiation is applied to the subject P at each imaging angle of the C-arm 12.

A plurality of radiographic image signals for the individual imaging angles obtained by the radiographic image obtaining unit 40 are inputted to the successive approximation reconstruction unit 41. Using the inputted radiographic image signals, the successive approximation reconstruction unit 41 performs reconstruction through a successive approximation process to generate a tomographic image of the subject. Specifically, in this embodiment, the ML-EM (Maximum Likelihood—Expectation Maximization) method, which is one of the successive approximation processes, is used. However, this is not intended to limit the invention, and the OS-EM (Ordered Subsets Expectation Maximization) method or the MAP-EM (Maximum A Posteriori—Expectation Maximization) method, or the other techniques, such as the ART (Algebraic Reconstruction Techniques), the SIRT (Simultaneous Interactive Reconstruction Techniques), the SART (Statistical Algebraic Reconstruction Techniques), the IRT (Iterative Reconstruction Techniques), or the like, may be used.

As mentioned above, the successive approximation reconstruction unit 41 performs an iteration using a successive approximation process. In this embodiment, a tomographic image generated by each iteration is sequentially outputted to the reconstructed image storing unit 42. That is, a tomographic image generated by the 1st iteration, a tomographic image generated by the 2nd iteration, a tomographic image generated by the 3rd iteration, . . . and a tomographic image generated by the M-th iteration are sequentially outputted to the reconstructed image storing unit 42.

The reconstructed image storing unit 42 stores the tomographic image of each iteration number sequentially outputted from the successive approximation reconstruction unit 41.

In the iteration number determining unit 43, iteration number determining regions, which are defined by segmenting a region, of which a tomographic image is generated, into a plurality of regions, are set in advance. The iteration number determining unit 43 obtains, for each iteration number determining region, information about degree of convergence of each iteration by using the tomographic image of each iteration number generated by the successive approximation reconstruction unit 41. Then, based on the obtained information about degree of convergence, the iteration number determining unit 43 determines the number of iterations for each iteration number determining region. In this embodiment, a mean value and a standard deviation are obtained as the information about degree of convergence of each iteration. A method for determining the number of iterations for each iteration number determining region will be described in detail later.

The region segmentation unit 44 obtains information about structure based on the tomographic images of a predetermined iteration number stored in the reconstructed image storing unit 42, and segments the region, of which a tomographic image is generated, into a plurality of segmented regions having different information about structure based on the obtained information about structure. Then, the region segmentation unit 44 outputs information of the segmented regions to the image combining unit 45. In this embodiment, information about edge is obtained as the information about structure. The information about edge includes not only information about an edge extending as a line but also information about a point structure.

As a method for obtaining the information about edge, an index value of the information about edge can be calculated based on primary differential values, secondary differential values or a standard deviation of the tomographic images of the predetermined iteration number, or pixel values of a filtered image obtained by applying band-pass filtering or high-pass filtering to the above tomographic image. With respect to the filtered image, images of different frequency bands, such as a Laplacian pyramid, may be used. With respect to a method for obtaining such an index value, a method for extracting a region including a structure, such as an edge or point, is known, and the detailed description thereof is omitted.

Then, the region segmentation unit 44 applies thresholding to the index value serving as the information about edge, which is calculated using the method as described above, to achieve the region segmentation. Specifically, in this embodiment, a first threshold and a second threshold, which is greater than the first threshold, are set. Then, if the index value is not greater than the first threshold, the region is determined as being a non-edge region, which includes relatively few edges and point structures. If the index value is greater than the second threshold, the region is determined as being an edge region, which includes relatively many edges and point structures. If the index value is greater than the first threshold and not greater than the second threshold, the region is determined as being a boundary region, which is a boundary between the edge region and the non-edge region.

While a region is segmented into three types of regions using the two thresholds in this embodiment, as described above, this is not intended to limit the invention. For example, only one threshold may be used to segment a region into two types of regions including the edge region and the non-edge region. Further, after a region is segmented into the two types of regions including the edge region and the non-edge region using only one threshold, a region including a boundary line therebetween and having a predetermined width may be redetermined as being the boundary region.

The method for determining the edge region is not limited to the above-described thresholding process, and a method using morphology processing may be used. The method for determining the edge region using the morphology processing is achieved by combining dilation and contraction of an image. This method is also known and the detailed description thereof is omitted. Regions detected by the morphology processing may be determined as being the edge regions, and the other regions may be determined as being the non-edge regions. Also in this case, after a region is segmented into the two types of regions including the edge region and the non-edge region, as described above, a region including a boundary line therebetween and having a predetermined width may be redetermined as being the boundary region.

Using the information of the edge region, the non-edge region and the boundary region outputted from the region segmentation unit 44, the number of iterations of each iteration number determining region determined by the iteration number determining unit 43, and the tomographic images of different iteration numbers stored in the reconstructed image storing unit 42, the image combining unit 45 generates a partial tomographic image for each segmented region by assigning a tomographic image of the iteration number (the number of iterations) of the iteration number determining region corresponding to the segmented region, and generates the entire tomographic image by combining the partial tomographic images of the segmented regions. A method for generating the partial tomographic image of each segmented region will be described in detail later.

The imaging control unit 46 controls driving of the rotating motion of the C-arm 12 by the rotation driving unit 15 and the timing of application of the radiation emitted from the radiation source 10. A specific control method will be described in detail later.

The monitor 31 displays a tomographic image or a three-dimensional image formed by a plurality of tomographic images based on the image signals representing the tomographic images of the subject outputted from the computer 30.

Next, operation of the radio tomographic imaging and displaying system of the first embodiment is described with reference to the flow chart shown in FIG. 3.

First, the subject P is placed on the bed 22, and the C-arm 12 is positioned such that the radiation source 10 and the radiation detector unit 11 are symmetrically positioned relative to the axis of rotation C, which is substantially the center of the body of the subject P. The C-arm 12 is moved based on operation of the computer 30 by the user.

Subsequently, the operator inputs imaging conditions via a predetermined input unit, and presses an imaging start button to input an instruction to start imaging. With this, the rotating motion of the C-arm 12 is started. When the C-arm 12 has reached each angle of rotation set in advance, the imaging control unit 46 outputs a control signal to the radiation source 10. In response to the control signal, radiation is emitted from the radiation source 10. The radiation transmitted through the subject P is detected by the radiographic image detector 11a, and the electric charge signals detected by the radiographic image detector 11a are read out. It should be noted that, in this embodiment, imaging operations are performed at angles of rotation of 4° pitch.

Then, the electric charge signals read out from the radiographic image detector 11a are subjected to predetermined processing by the signal processing unit 11b and are outputted to the computer 30, so that the radiographic image signal for each angle of rotation is obtained by the radiographic image obtaining unit 40 (S10). When the imaging angle has reached an end-of-imaging angle, the rotation of the C-arm 12 is stopped and the series of imaging operations end.

The radiographic image signals for the individual angles of rotation obtained by the radiographic image obtaining unit 40 are sequentially outputted to the successive approximation reconstruction unit 41. The successive approximation reconstruction unit 41 performs the 1st iteration on the radiographic image signals inputted thereto to generate a tomographic image (S12). The tomographic image generated by the 1st iteration is outputted to and stored in the reconstructed image storing unit 42 (S14).

Then, the tomographic image of the 1st iteration stored in the reconstructed image storing unit 42 is outputted to the iteration number determining unit 43. As described above, the iteration number determining regions, which are defined by segmenting a region, of which a tomographic image is generated, into a plurality of regions, are set in advance in the iteration number determining unit 43. In this embodiment, iteration number determining regions defined by segmenting a region, of which a tomographic image is generated, into a rectangular mesh pattern, as shown in FIG. 4, are set in advance. It should be noted that the manner of setting the iteration number determining regions is not limited to this example, and the iteration number determining regions may be defined by segmenting a region into a mesh pattern other than a rectangular mesh pattern, for example.

Then, the iteration number determining unit 43 calculates, for each iteration number determining region set in advance, a mean value and a standard deviation of a tomographic image in the region (S16). Then, whether or not the mean value and the standard deviation of each iteration number determining region have been converged is determined, respectively (S18 to S26).

Figure 5:
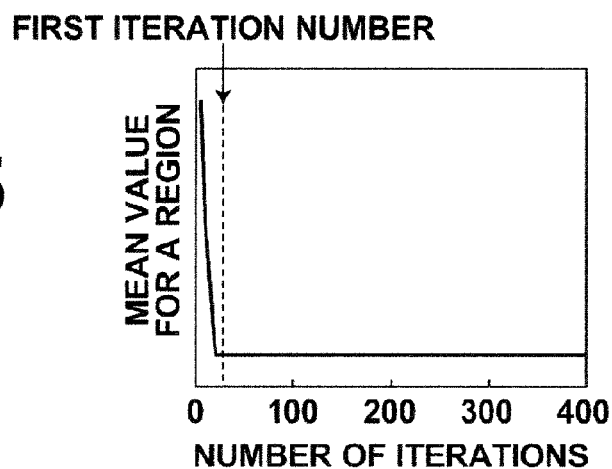
FIG. 5 is a diagram for explaining a method for determining a first iteration number based on a degree of convergence of mean value.
Figure 6:
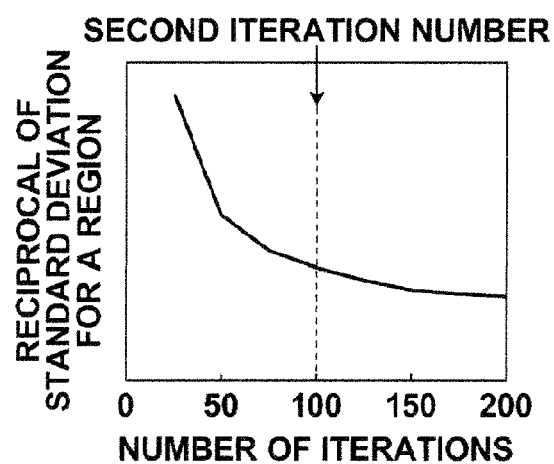
FIG. 6 is a diagram for explaining a method for determining a second iteration number based on a degree of convergence of standard deviation.

In this embodiment, the determination as to whether or not the mean value has been converged is achieved by plotting, for each iteration number determining region, the mean values along the vertical axis and the iteration numbers along the horizontal axis, as shown in FIG. 5, and determining when the inclination of the graph of the plotted mean values has become smaller than a predetermined threshold. The determination as to whether or not the standard deviation has been converged is achieved by plotting, for each iteration number determining region, reciprocals of the standard deviations along the vertical axis and the iteration numbers along the horizontal axis, as shown in FIG. 6, and determining when the inclination of the graph of the plotted reciprocals of the standard deviations has become smaller than a predetermined threshold.

It should be noted that, since the current tomographic image is that of the 1st iteration, the mean value and the standard deviation thereof have naturally not been converged. Therefore, signals indicating that the mean value and the standard deviation have not been converged are outputted to the successive approximation reconstruction unit 41. Then, the successive approximation reconstruction unit 41 performs the 2nd iteration (S12), and the tomographic image of the 2nd iteration is stored in the reconstructed image storing unit 42 and is again inputted to the iteration number determining unit 43.

Again, the iteration number determining unit 43 calculates a mean value and a standard value of the tomographic image for each iteration number determining region, and the iteration number determining unit 43 determines, for each iteration number determining region, whether or not the mean value and the standard deviation have been converged, as described above.

The iteration by the successive approximation reconstruction unit 41 and the determination as to whether or not the mean value and the standard deviation have been converged are repeated in the same manner as described above, until the mean value and the standard deviation of each iteration number determining region are converged. Then, when the mean value of a given iteration number determining region, for example, has been converged (S18, YES), the iteration number of the tomographic image with the converged mean value is saved as a candidate of the first iteration number of the given iteration number determining region (S20). Similarly, when the reciprocal of the standard deviation of a given iteration number determining region, for example, has been converged (S22, YES), the iteration number of the tomographic image with the converged standard deviation is saved as a candidate of the second iteration number of the given iteration number determining region (S24).

The iteration number determining unit 43 sequentially determines whether or not the mean values and the standard deviations of all the iteration number determining regions have been converged (S26). It should be noted that, in general, the convergence of the standard deviation is slower than the convergence of the mean value, and therefore the second iteration number becomes greater than the first iteration number. Therefore, finally, only the determination as to whether or not the standard deviation has been converged is performed.

If there still remains an iteration number determining region, of which the standard deviation has not yet been converged, then, whether or not the current iteration number of interest is not greater than a predetermined upper limit, which is set in advance, is determined (S28).

If the iteration number of the current tomographic image of interest has not reached the predetermined upper limit, the successive approximation reconstruction unit 41 again repeats the iteration, and determines whether or not the standard deviations of all the iteration number determining regions have been converged. In contrast, if there still remains an iteration number determining region, of which the standard deviation has not yet been converged, and the iteration number of the current tomographic image of interest has reached the predetermined upper limit, the iteration number of the upper limit is determined as the second iteration number of the iteration number determining region, of which the standard deviation has not yet been converged (S32). With respect to the other iteration number determining regions, of which the mean value and the standard deviation have already been converged, the candidates of the first and second iteration numbers that have already been saved when the iteration number has reached the upper limit are determined as the final first and second iteration numbers.

In contrast, if the mean values and the standard deviations of all the iteration number determining regions are converged before the iteration number exceeds the upper limit (S26, NO), then, whether or not the candidate of the first iteration number saved for each iteration number determining region is smaller than a predetermined lower limit, which is set in advance, is determined (S30).

If the candidate of the first iteration number saved for each iteration number determining region is not smaller than the predetermined lower limit, then, the iteration performed by the successive approximation reconstruction unit 41 ends, and the currently saved candidates of the first and second iteration numbers of each iteration number determining region are determine as the final first and second iteration numbers. In contrast, if there is an iteration number determining region which has the currently saved candidate of the first iteration number smaller than a predetermined lower limit, the iteration number of the lower limit is determined as the final first iteration number for the iteration number determining region. With respect to the other iteration number determining regions, the currently saved first iteration numbers are determined as the final first iteration numbers. Further, if there is an iteration number determining region which has the currently saved candidate of the second iteration number smaller than a predetermined lower limit, the iteration by the successive approximation reconstruction unit 41 is again repeated until the iteration number reaches the lower limit, and the iteration number of the lower limit is determined as the final second iteration number for the iteration number determining region. With respect to the other iteration number determining regions, the currently saved second iteration numbers are determined as the final second iteration numbers (S32).

As described above, the iteration number determining unit 43 determines the first and second iteration numbers for each iteration number determining region, and outputs the information thereof to the image combining unit 45. It should be noted that, in the case where the first and second iteration numbers are determined as described above, the successive approximation reconstruction unit 41 ends the iteration of the successive approximation process when the second iteration numbers of all the iteration number determining regions have been determined.

Then, the tomographic images that are generated when the first and second iteration numbers are determined, as described above, are outputted from the reconstructed image storing unit 42 to the region segmentation unit 44. The region segmentation unit 44 calculates the edge information of the inputted tomographic images, and extracts the above-described three types of regions including the edge region, the non-edge region and the boundary region based on the edge information to achieve the region segmentation (S34). Then, the information of the regions is outputted from the region segmentation unit 44 to the image combining unit 45. As the tomographic image used by the region segmentation unit 44 to extract the three types of regions, it is desirable to use a tomographic image having the largest second iteration number among the tomographic images that are stored in the reconstructed image storing unit 42 when the first and second iteration numbers of all the iteration number determining regions have been determined. However, this is not intended to limit the invention, and a different one of the tomographic images may be used.

Subsequently, the image combining unit 45 generates a partial tomographic image of each region based on the information of the edge region, the non-edge region and the boundary region and the information of the first and second iteration numbers of each iteration number determining region inputted thereto, and combines the partial tomographic images to generate a final tomographic image (S36).

Figure 7:
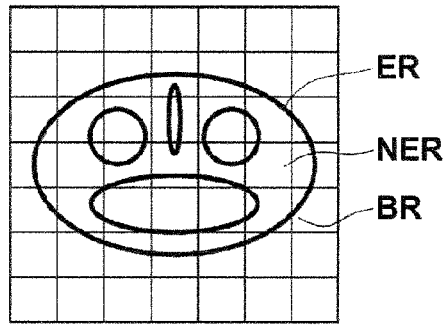
FIG. 7 is a diagram illustrating one example of edge regions ER, non-edge regions NER and boundary regions BR.

FIG. 7 is a diagram showing one example of edge regions ER (black line portions), non-edge regions NER (white portions) and boundary regions BR (gray portions). Specifically, for example, for an area of the edge region ER, the image combining unit 45 generates a partial tomographic image by assigning the tomographic image of the second iteration number of the iteration number determining region corresponding to the edge region ER. For an area of the non-edge region NER, the image combining unit 45 generates a partial tomographic image by assigning the tomographic image of the first iteration number of the iteration number determining region corresponding to the non-edge region NER. For an area of the boundary region BR, the image combining unit 45 generates a partial tomographic image by assigning a tomographic image of an iteration number which is an average value of the first iteration number and the second iteration number of the iteration number determining region corresponding to the boundary region BR. Generating the partial tomographic images in this manner allows assigning tomographic images of different iteration numbers to the edge region ER, the non-edge region NER and the boundary region BR. Further, since different iteration number determining regions may have different first and second iteration numbers determined therefor, as described above, tomographic images of different iteration numbers may be assigned to the same type of regions. It should be noted that the tomographic images of the first and second iteration numbers are read out as necessary from the reconstructed image storing unit 42.

While the partial tomographic image for an area of the boundary region BR is generated by assigning a tomographic image of an iteration number which is an average value of the first iteration number and the second iteration number in the above description, this is not intended to limit the invention. The partial tomographic image for an area of the boundary region BR may be generated by assigning a tomographic image of a certain iteration number that is greater than the first iteration number and smaller than the second iteration number, such as a tomographic image of an iteration number nearer to one of the first and second iteration numbers.

Further, as a method for assigning a tomographic image to the boundary region BR, for example, a distance between the edge region and the non-edge region may be calculated for each partial region (which may be each pixel) in the boundary region BR, and the iteration number of a tomographic image to be assigned to the partial region may be set depending on the distance. Specifically, a tomographic image of an iteration number nearer to the second iteration number is assigned to a partial region nearer to the edge region, and a tomographic image of an iteration number nearer to the first iteration number is assigned to a partial region nearer to the non-edge region. Specifically, for example, assuming that the distance from the edge region to a given pixel in the boundary region is A, the distance from the non-edge region to the pixel is B, the first iteration number is N1 and the second iteration number is N2, an iteration number n for the pixel is calculated based on the equation below:

$$n=(B{\times}N2+A{\times}N1)/(A+B).$$

It should be noted that the distance from the edge region to the pixel herein is the shortest distance from the boundary line between the edge region and the boundary region to the pixel, and the distance from the non-edge region to the pixel is the shortest distance from the boundary line between the non-edge region and the boundary region to the pixel.

Alternatively, an edge likelihood index value of each partial region (which may be each pixel) in the boundary region BR may be used to determine the iteration number for the partial region based on the index value. It should be noted that this method is employed in the case where the region segmentation unit 44 performs the region segmentation using edge likelihood index values.

Specifically, when the edge likelihood index value of a partial region (which may be a pixel) in the boundary region BR is nearer to the first threshold used for the region segmentation, a tomographic image of an iteration number nearer to the first iteration number is assigned to the partial region, and when the edge likelihood index value of a partial region in the boundary region BR is nearer to the second threshold used for the region segmentation, a tomographic image of an iteration number nearer to the second iteration number is assigned to the partial region.

Specifically, for example, assuming that the edge likelihood index value of a given pixel in the boundary region is T, the first threshold is T1, the second threshold is T2, the first iteration number is N1 and the second iteration number is N2, an iteration number n for the pixel is calculated based on the equation below:

$$n=\{(T-T1){\times}N2+(T2-T){\times}N1\}/(T2-T1).$$

Still alternatively, to each partial region (which may be each pixel) in the boundary region BR, a tomographic image resulting from weighted sum of the tomographic image of the first iteration number and the tomographic image of the second iteration number depending on the distance from the edge region and the distance from the non-edge region may be assigned. A larger weight on the tomographic image of the second iteration number is set for a partial region nearer to the edge region, and a larger weight on the tomographic image of the first iteration number is set for a partial region nearer to the non-edge region. Specifically, for example, assuming that the distance from the edge region to a given pixel in the boundary region is A, the distance from the non-edge region to the pixel is B, the pixel value of the tomographic image of the first iteration number is P1 and the pixel value of the tomographic image of the second iteration number is P2, a pixel value p of the pixel is calculated based on the following equation:

$$p=(B{\times}P2+A{\times}P1)/(A+B)$$

Yet alternatively, the edge likelihood index value of each partial region (which may be each pixel) in the boundary region BR may be used, and a tomographic image resulting from weighted sum of the tomographic image of the first iteration number and the tomographic image of the second iteration number depending on the index value may be assigned. A larger weight on the tomographic image of the second iteration number is set for an index value nearer to the first threshold used for the region segmentation, and a larger weight on the tomographic image of the first iteration number is set for an index value nearer to the second threshold used for the region segmentation.

Specifically, for example, assuming that the edge likelihood index value of a given pixel in the boundary region is T, the first threshold is T1, the second threshold is T2, the pixel value of the tomographic image of the first iteration number is P1 and the pixel value the tomographic image of the second iteration number is P2, a pixel value p of the pixel is calculated based on the following equation:

$$p=\{(T-T1){\times}P2+(T2-T){\times}P1\}/(P2-P1)$$

Then, the image signal of the tomographic image generated by the image combining unit 45, as described above, is outputted to the monitor 31, and a tomographic image or a three-dimensional image formed by a plurality of tomographic images is displayed on the monitor 31 based on the image signal.

Next, a radio tomographic imaging and displaying system employing a radio tomographic image generation device according to a second embodiment of the invention is described. The entire schematic configuration of the radio tomographic imaging and displaying system employing the second embodiment is the same as the entire schematic configuration of the first embodiment shown in FIG. 1, and the internal configuration of the computer is different. Specifically, in the first embodiment, the iteration number determining regions set in advance are segmented regions in a mesh pattern. In the second embodiment, the edge region, the non-edge region and the boundary region are set as the iteration number determining regions. That is, in the second embodiment, the iteration number determining regions used to determine the above-described first and second iteration numbers are the same as the segmented regions used to assign the tomographic image of the first iteration number or the tomographic image of the second iteration number.

Figure 8:
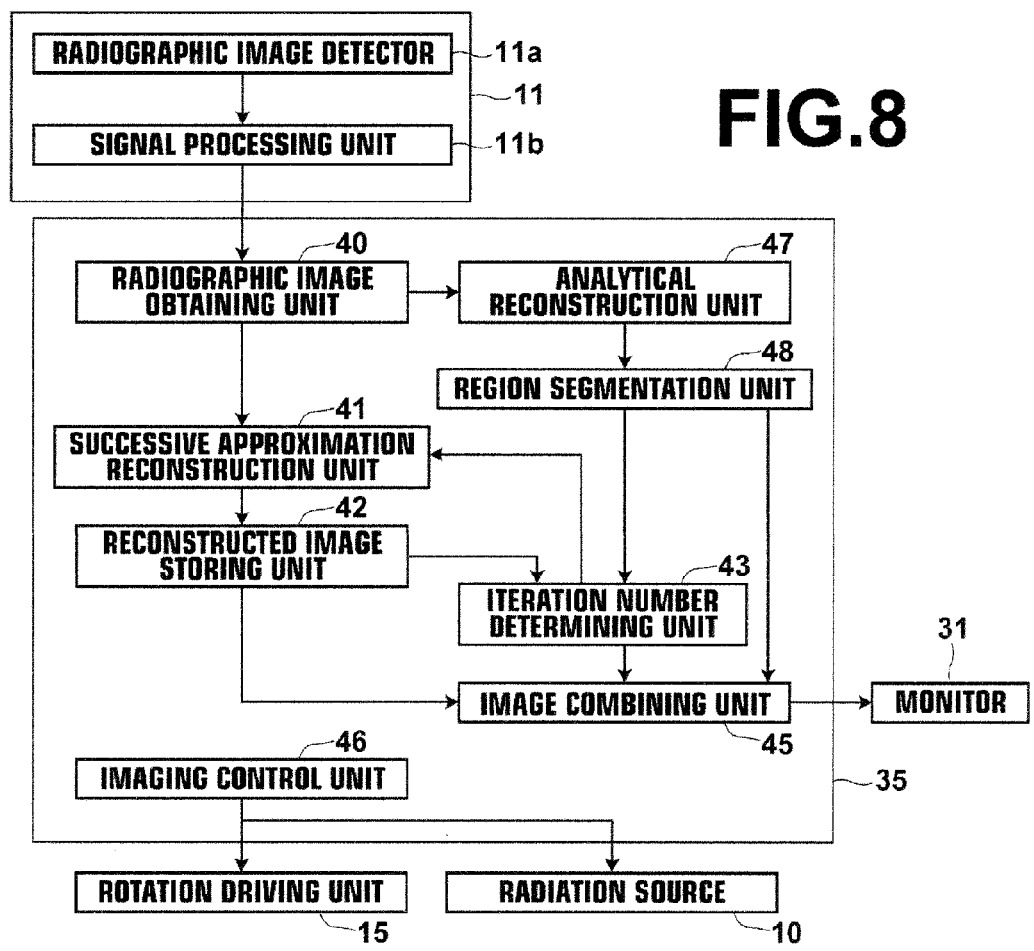
FIG. 8 is a block diagram illustrating the internal configuration of a computer of a radio tomographic imaging and displaying system employing a radio tomographic imaging device according to a second embodiment of the invention.

FIG. 8 is a block diagram illustrating the internal configuration of a computer 35 of the radio tomographic imaging and displaying system employing the second embodiment. The computer 35 of the second embodiment further includes an analytical reconstruction unit 47, which generates a tomographic image of the subject by performing reconstruction using an analytical method based on the radiographic image signals for the individual angles of rotation obtained by the radiographic image obtaining unit 40. The region segmentation unit 48 performs the region segmentation into the edge region, the non-edge region and the boundary region based on the tomographic image generated by the analytical reconstruction unit 47. The edge region, the non-edge region and the boundary region segmented by the region segmentation unit 48 are used as the iteration number determining regions, and are also used to assign the tomographic image of the first iteration number or the tomographic image of the second iteration number.

Specifically, in this embodiment, the analytical reconstruction unit 47 uses the FBP (Filter Back Projection) method as the analytical reconstruction method to generate the tomographic image. It should be noted that, while the FBP method is used in this embodiment, any other analytical reconstruction method, such as the FFT (Fast Fourier Transform) method or the convolution method, may be used.

The other features are generally the same as those of the first embodiment.

Next, operation of the radio tomographic imaging and displaying system of the second embodiment is described with reference to the flow chart shown in FIG. 9.

In the radio tomographic imaging and displaying system of the second embodiment, a radiographic image is taken at each angle of rotation in the same manner as in the first embodiment, and radiographic image signals for the individual angles of rotation are obtained by the radiographic image obtaining unit 40 (S40).

Then, the radiographic image signals for the individual angles of rotation obtained by the radiographic image obtaining unit 40 are outputted to the analytical reconstruction unit 47, and the analytical reconstruction unit 47 generates a tomographic image based on the inputted radiographic image signals using the FBP method (S42).

The tomographic image generated by the analytical reconstruction unit 47 is outputted to the region segmentation unit 48. The region segmentation unit 48 extracts the edge region, the non-edge region and the boundary region from the tomographic images inputted thereto, and outputs the information thereof to the iteration number determining unit 43 and the image combining unit 45 (S44). The method for extracting the edge region, the non-edge region and the boundary region is the same as that described in the first embodiment.

The radiographic image signals for the individual angles of rotation obtained by the radiographic image obtaining unit 40 are also outputted to the successive approximation reconstruction unit 41. The successive approximation reconstruction unit 41 performs the 1st iteration on the radiographic image signals inputted thereto to generate a tomographic image (S46), and the tomographic image of the 1st iteration is outputted to and stored in the reconstructed image storing unit 42 (S48).

Then, the tomographic image of the 1st iteration stored in the reconstructed image storing unit 42 is outputted to the iteration number determining unit 43.

As described above, the information of the edge region, the non-edge region and the boundary region has been inputted to the iteration number determining unit 43 in advance, and the edge region, the non-edge region and the boundary region are set as the iteration number determining regions. The iteration number determining unit 43 calculates a mean value and a standard deviation of the tomographic image within each of the iteration number determining regions set in advance (S50).

Then, similarly to the first embodiment, the iteration number determining unit 43 determines whether or not the mean value and the standard deviation of each iteration number determining region have been converged, respectively (S52 to S60), and determines whether or not the iteration number of the current tomographic image of interest has reached the predetermined upper limit or whether or not the iteration number of the current tomographic image of interest is greater than the predetermined lower limit (362, S64) to determine the first and second iteration numbers for each iteration number determining region (S66). It should be noted that the operations in S52 to S66 are the same as the operations in S18 to S32 shown in FIG. 3 described in the first embodiment, and therefore the explanation thereof is omitted.

Then, the iteration number determining unit 43 outputs the information of the first and second iteration numbers determined for each iteration number determining region to the image combining unit 45. That is, the information of the first and second iteration numbers determined for each of the edge region, the non-edge region and the boundary region is outputted to the image combining unit 45.

Subsequently, the image combining unit 45 generates a partial tomographic image of each region based on the information of the edge region, the non-edge region and the boundary region and the information of the first and second iteration numbers corresponding to the edge region, the non-edge region and the boundary region inputted thereto, and combines the partial tomographic images to generate a final tomographic image (S68).

Specifically, for example, for an area of the edge region ER, the image combining unit 45 generates the partial tomographic image by assigning the tomographic image of the second iteration number determined for the edge region ER. For an area of the non-edge region NER, the image combining unit 45 generates the partial tomographic image by assigning the tomographic image of the first iteration number determined for the non-edge region NER. For an area of the boundary region BR, the image combining unit 45 generates the partial tomographic image by assigning a tomographic image of an iteration number which is an average value of the first iteration number and the second iteration number determined for the boundary region BR. Generating the partial tomographic images in this manner allows assigning tomographic images of different iteration numbers to the edge region ER, the non-edge region NER and the boundary region BR. It should be noted that the tomographic images of the first and second iteration numbers are read out as necessary from the reconstructed image storing unit 42.

The method for assigning the tomographic image to the boundary region BR is not limited to the above-described method, and a different assigning method, such as those described in the first embodiment, may be employed.

While the iteration number of the tomographic image to be assigned to each of the edge region, the non-edge region and the boundary region is determined using the first and second iteration numbers determined for each iteration number determining region in the above-described first and second embodiments, this is not intended to limit the invention. For example, a mean value, a maximum value or a minimum value of the first iteration numbers determined for the individual iteration number determining regions may be determined as the final first iteration number, and a mean value, a maximum value or a minimum value of the second iteration numbers determined for the individual iteration number determining regions may be determined as the final second iteration number. Then, the iteration number of the tomographic image to be assigned to each of the edge region, the non-edge region and the boundary region may be determined using the finally determined first and second iteration numbers.

According to the radio tomographic imaging and displaying systems of the first and second embodiments, a plurality of tomographic images of different iteration numbers are generated by the successive approximation process, and a region, of which a tomographic image is generated, are segmented into the edge region, the non-edge region and the boundary region. Then, for the individual regions, partial tomographic images using reconstructed images of different iteration numbers are generated, and the generated partial tomographic images for the individual regions are used to generate a tomographic image of the subject. This allows, for example, assigning the reconstructed image of a relatively large iteration number to the segmented region that includes small structures and assigning the reconstructed image of a relatively small iteration number to the segmented region that is a flat area, thereby allowing generation of a tomographic image having improved sharpness and contrast of small structures and improved S/N ratio of flat areas.

While the radio tomographic imaging device of the invention is applied to a radio tomographic imaging and displaying system for taking tomographic images of the head or chest of a subject in the above-described embodiments, the subject is not limited to the head or chest. For example, the radio tomographic imaging device of the invention may be applied to a radio tomographic imaging and displaying system for taking tomographic images of the breast of a subject.

What is claimed is:

1. A radio tomographic image generation device comprising:
    a radiographic image obtaining unit, wherein at least one of a radiation source and a radiographic image detector for detecting radiation emitted from the radiation source and transmitted through a subject to output a radiographic image signal representing a radiographic image of the subject is made to orbit around the subject to obtain the radiographic image signal for each predetermined imaging angle outputted from the radiographic image detector when the radiation is applied to the subject at the predetermined imaging angle; and
    a tomographic image generation unit for generating a tomographic image of the subject by performing reconstruction using a successive approximation process based on the radiographic image signals for the individual imaging angles obtained by the radiographic image obtaining unit,
    wherein the tomographic image generation unit comprises:
    a reconstruction unit for generating a plurality of reconstructed images of different iteration numbers of the successive approximation process;
    a region segmentation unit for obtaining information about structure based on the radiographic image signals and segmenting, based on the information about structure, a region, of which the tomographic image is generated, into a plurality of segmented regions having different information about structure; and
    an image combining unit for generating partial tomographic images by using the reconstructed images of different iteration numbers for the individual segmented regions segmented by the segmentation unit based on the information about structure of the individual segmented regions, and generating the tomographic image of the subject by using the generated partial tomographic images for the individual segmented regions.

2. The radio tomographic image generation device as claimed in claim 1, wherein
    the information about structure is edge information, and
    the region segmentation unit calculates an edge likelihood index value based on the edge information, determines a region as being an edge region if the index value of the region is greater than a predetermined threshold, determines a region as a non-edge region if the index value of the region is not greater than the threshold, and performs the region segmentation wherein the segmented regions are the edge region and the non-edge region.

3. The radio tomographic image generation device as claimed in claim 1, wherein
    the information about structure represents an edge structure detected by a morphology operation, and
    the region segmentation unit determines a region of the edge structure as being an edge region, determines a region other than the region of the edge structure as being a non-edge region, and performs the region segmentation wherein the segmented regions are the edge region and the non-edge region.

4. The radio tomographic image generation device as claimed in claim 2, wherein the region segmentation unit determines a region including a boundary line between the edge region and the non-edge region and having a predetermined width as being a boundary region, and performs the region segmentation wherein the segmented regions are the edge region, the non-edge region and the boundary region.

5. The radio tomographic image generation device as claimed in claim 1, wherein
    the information about structure is edge information, and
    the region segmentation unit calculates an edge likelihood index value based on the edge information, determines a region as being a non-edge region if the index value of the region is not greater than a first threshold, determines a region as being an edge region if the index value of the region is greater than a second threshold, which is greater than the first threshold, determines a region as being a boundary region if the index value of the region is greater than the first threshold and not greater than the second threshold, and performs the region segmentation wherein the segmented regions are the edge region, the non-edge region and the boundary region.

6. The radio tomographic image generation device as claimed in claim 2, wherein
    the tomographic image generation unit further comprises an iteration number determining unit, the iteration number determining unit including a plurality of iteration number determining regions set therein, the iteration number determining regions being defined by segmenting a region, of which the tomographic image is generated, into a plurality of regions, and the iteration number determining regions being used for determining the iteration numbers of the reconstructed images used to generate the partial tomographic images, wherein the iteration number determining unit obtains, for each iteration number determining region, information about degree of convergence of the iteration by using the reconstructed images generated by the reconstruction unit, and determines, based on the obtained information about degree of convergence, the iteration number of the reconstructed image used to generate the partial tomographic image for each iteration number determining region, and
    wherein the image combining unit generates the partial tomographic image for each segmented region based on the reconstructed image of the iteration number determined for the iteration number determining region corresponding to the segmented region.

7. The radio tomographic image generation device as claimed in claim 6, wherein
    the iteration number determining unit obtains a plurality of pieces of the information about degree of convergence for each iteration number determining region, and determines a first iteration number and a second iteration number greater than the first iteration number based on the obtained prices of the information about degree of convergence, and
    the image combining unit generates the partial tomographic image of each segmented region by using the reconstructed image of an iteration number not smaller than the first iteration number and not greater than the second iteration number determined for the iteration number determining region corresponding to the segmented region.

8. The radio tomographic image generation device as claimed in claim 7, wherein
    the pieces of information about degree of convergence are pieces of information about degree of convergence of mean value and degree of convergence of standard deviation of the individual reconstructed images in the iteration number determining region, and the iteration number determining unit determines the first iteration number based on the pieces of information about degree of convergence of mean value, and determines the second iteration number based on the pieces of information about degree of convergence of standard deviation.

9. The radio tomographic image generation device as claimed in claim 7, wherein the image combining unit generates the partial tomographic image for the segmented region which is the edge region by using the reconstructed image of the second iteration number, and generates the partial tomographic image for the segmented region which is the non-edge region by using the reconstructed image of the first iteration number.

10. The radio tomographic image generation device as claimed in claim 4, wherein
the tomographic image generation unit further comprises an iteration number determining unit, the iteration number determining unit including a plurality of iteration number determining regions set therein, the iteration number determining regions being defined by segmenting a region, of which the tomographic image is generated, into a plurality of regions, and the iteration number determining regions being used for determining the iteration numbers of the reconstructed images used to generate the partial tomographic images, wherein the iteration number determining unit obtains, for each iteration number determining region, information about degree of convergence of the iteration by using the reconstructed images generated by the reconstruction unit, and determines, based on the obtained information about degree of convergence, the iteration number of the reconstructed image used to generate the partial tomographic image for each iteration number determining region, and
wherein the image combining unit generates the partial tomographic image for each segmented region based on the reconstructed image of the iteration number determined for the iteration number determining region corresponding to the segmented region.

11. The radio tomographic image generation device as claimed in claim 10, wherein
the iteration number determining unit obtains a plurality of pieces of the information about degree of convergence for each iteration number determining region, and determines a first iteration number and a second iteration number greater than the first iteration number based on the obtained pieces of information about degree of convergence, and
the image combining unit generates the partial tomographic image of each segmented region by using the reconstructed image of an iteration number not smaller than the first iteration number and not greater than the second iteration number determined for the iteration number determining region corresponding to the segmented region.

12. The radio tomographic image generation device as claimed in claim 11, wherein
the pieces of information about degree of convergence are pieces of information about degree of convergence of mean value and degree of convergence of standard deviation of the individual reconstructed images in the iteration number determining region, and
the iteration number determining unit determines the first iteration number based on the pieces of information about degree of convergence of mean value, and determines the second iteration number based on the pieces of information about degree of convergence of standard deviation.

13. The radio tomographic image generation device as claimed in claim 11, wherein the image combining unit generates the partial tomographic image for the segmented region which is the edge region by using the reconstructed image of the second iteration number, generates the partial tomographic image for the segmented region which is the non-edge region by using the reconstructed image of the first iteration number, and generates the partial tomographic image for the segmented region which is the boundary region by using the reconstructed image of an iteration number smaller than the second iteration number and greater than the first iteration number.

14. The radio tomographic image generation device as claimed in claim 11, wherein the image combining unit generates the partial tomographic image for the segmented region which is the edge region by using the reconstructed image of the second iteration number, generates the partial tomographic image for the segmented region which is the non-edge region by using the reconstructed image of the first iteration number, and generates the partial tomographic image for the segmented region which is the boundary region by using the reconstructed image of an iteration number nearer to the second iteration number for the boundary region nearer to the edge region or using the reconstructed image of an iteration number nearer to the first iteration number for the boundary region nearer to the non-edge region.

15. The radio tomographic image generation device as claimed in claim 11, wherein the image combining unit generates the partial tomographic image for the segmented region which is the edge region by using the reconstructed image of the second iteration number, generates the partial tomographic image for the segmented region which is the non-edge region by using the reconstructed image of the first iteration number, and generates the partial tomographic image for the segmented region which is the boundary region by using a reconstructed image resulting from weighted sum of the tomographic image of the first iteration number and the tomographic image of the second iteration number with setting a larger weight on the tomographic image of the second iteration number for the boundary region nearer to the edge region or setting a larger weight on the tomographic image of the first iteration number for the boundary region nearer to the non-edge region.

16. The radio tomographic image generation device as claimed in claim 5, wherein
the tomographic image generation unit further comprises an iteration number determining unit, the iteration number determining unit including a plurality of iteration number determining regions set therein, the iteration number determining regions being defined by segmenting a region, of which the tomographic image is generated, into a plurality of regions, and the iteration number determining regions being used for determining the iteration numbers of the reconstructed images used to generate the partial tomographic images, wherein the iteration number determining unit obtains, for each iteration number determining region, information about degree of convergence of the iteration by using the reconstructed images generated by the reconstruction unit, and determines, based on the obtained information about degree of convergence, the iteration number of the reconstructed image used to generate the partial tomographic image for each iteration number determining region, and wherein the image combining unit generates the partial tomographic image for each segmented region based on the reconstructed image of the iteration number determined for the iteration number determining region corresponding to the segmented region.

17. The radio tomographic image generation device as claimed in claim 16, wherein
the iteration number determining unit obtains a plurality of pieces of the information about degree of convergence for each iteration number determining region, and determines a first iteration number and a second iteration number greater than the first iteration number based on the obtained pieces of information about degree of convergence, and
the image combining unit generates the partial tomographic image of each segmented region by using the reconstructed image of an iteration number not smaller than the first iteration number and not greater than the second iteration number determined for the iteration number determining region corresponding to the segmented region.

18. The radio tomographic image generation device as claimed in claim 16, wherein
the pieces of information about degree of convergence are pieces of information about degree of convergence of mean value and degree of convergence of standard deviation of the individual reconstructed images in the iteration number determining region, and
the iteration number determining unit determines the first iteration number based on the pieces of information about degree of convergence of mean value, and determines the second iteration number based on the pieces of information about degree of convergence of standard deviation.

19. The radio tomographic image generation device as claimed in claim 17, wherein the image combining unit generates the partial tomographic image for the segmented region which is the edge region by using the reconstructed image of the second iteration number, generates the partial tomographic image for the segmented region which is the non-edge region by using the reconstructed image of the first iteration number, and generates the partial tomographic image for the segmented region which is the boundary region by using a reconstructed image of an iteration number nearer to the first iteration number for the boundary region with the index value nearer to the first threshold or using a reconstructed image of an iteration number nearer to the second iteration number for the boundary region with the index value nearer to the second threshold.

20. The radio tomographic image generation device as claimed in claim 17, wherein the image combining unit generates the partial tomographic image for the segmented region which is the edge region by using the reconstructed image of the second iteration number, generates the partial tomographic image for the segmented region which is the non-edge region by using the reconstructed image of the first iteration number, and generates the partial tomographic image for the segmented region which is the boundary region by using a reconstructed image resulting from weighted sum of the tomographic image of the first iteration number and the tomographic image of the second iteration number with setting a larger weight on the reconstructed image of the first iteration number for the boundary region with the index value nearer to the first threshold or setting a larger weight on the reconstructed image of the first iteration number for the boundary region with the index value nearer to the second threshold.

21. The radio tomographic image generation device as claimed in claim 7, wherein the region segmentation unit obtains the edge information based on the reconstructed image of the second iteration number.

22. The radio tomographic image generation device as claimed in claim 7, wherein the first and second iteration numbers are determined such that the first iteration number is not smaller than a predetermined lower limit and the second iteration number is not greater than a predetermined upper limit.

23. The radio tomographic image generation device as claimed in claim 7, wherein the reconstruction unit ends the iteration when the second iteration numbers have been determined during generation of the reconstructed images forming the partial tomographic images of the individual segmented regions.

24. The radio tomographic image generation device as claimed in claim 7, wherein the iteration number determining unit determines a candidate of the first iteration number and a candidate of the second iteration number for each of the iteration number determining regions, and then determines a mean value, a maximum value or a minimum value of the candidates of the first iteration number of the individual iteration number determining regions as the first iteration number and a mean value, a maximum value or a minimum value of the candidates of the second iteration number of the individual iteration number determining regions as the second iteration number.

25. The radio tomographic image generation device as claimed in claim 6, wherein the iteration number determining regions are regions defined by segmenting a region, of which the tomographic image is generated, into a mesh pattern.

26. The radio tomographic image generation device as claimed in claim 1, wherein the region segmentation unit obtains the information about structure based on the reconstructed images obtained by an analytical method using the radiographic image signals.

27. The radio tomographic image generation device as claimed in claim 2, wherein the edge information is calculated from primary differential values, secondary differential values, a standard deviation, values resulting from band-pass filtering or values resulting from high-pass filtering.

28. A radio tomographic image generation method, wherein at least one of a radiation source and a radiographic image detector for detecting radiation emitted from the radiation source and transmitted through a subject to output a radiographic image signal representing a radiographic image of the subject is made to orbit around the subject to obtain the radiographic image signal for each predetermined imaging angle outputted from the radiographic image detector when the radiation is applied to the subject at the predetermined imaging angle, and a tomographic image of the subject is generated by performing reconstruction using a successive approximation process based on the radiographic image signals for the individual imaging angles, the method comprising:
generating a plurality of reconstructed images of different iteration numbers of the successive approximation process;
segmenting, based on the radiographic image signals, a region, of which the tomographic image is generated, into a plurality of segmented regions having different information about structure;
generating partial tomographic images by using the reconstructed images of different iteration numbers for the individual segmented regions based on the information about structure of the individual segmented regions; and generating the tomographic image of the subject by using the generated partial tomographic images for the individual segmented regions.

\* \* \* \* \*